United States Patent
Xiong et al.

(10) Patent No.: US 8,524,228 B2
(45) Date of Patent: Sep. 3, 2013

(54) NETRIN-1 COMPOSITIONS AND METHODS OF USE THEREOF

(75) Inventors: Wen-Cheng Xiong, Evans, GA (US); Jae-Ho Lee, Augusta, GA (US); Lin Mei, Evans, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 484 days.

(21) Appl. No.: 12/740,594

(22) PCT Filed: Nov. 3, 2008

(86) PCT No.: PCT/US2008/082238
§ 371 (c)(1),
(2), (4) Date: Apr. 29, 2010

(87) PCT Pub. No.: WO2009/059289
PCT Pub. Date: May 7, 2009

(65) Prior Publication Data
US 2010/0260774 A1    Oct. 14, 2010

Related U.S. Application Data

(60) Provisional application No. 61/001,580, filed on Nov. 2, 2007.

(51) Int. Cl.
*A61K 39/395* (2006.01)
*A61K 39/00* (2006.01)
*C07K 16/22* (2006.01)

(52) U.S. Cl.
USPC ............... 424/130.1; 424/133.1; 530/387.1; 530/388.23; 530/388.24; 514/841

(58) Field of Classification Search
None
See application file for complete search history.

(56) References Cited

U.S. PATENT DOCUMENTS

2006/0025335 A1    2/2006    Kinane
2006/0153840 A1*   7/2006    Eichmann et al. ......... 424/143.1

FOREIGN PATENT DOCUMENTS

WO    WO2005/074556    *    8/2005

OTHER PUBLICATIONS

McLachlan et al., "Hormonal Regulation of Spermatogenesis," Copyright 2002 by The Endocrine Society; pp. 149-179.*
Sitruk-Ware et al., Sep. 17, 2012. pii: S0010-7824(12)00729-9. doi: 10.1016/j.contraception.2012.08.002. [Epub ahead of print].*
Wells, 1990, Biochemistry 29: 8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14: 248-250.*
Smith et al., 1997, Nature Biotechnology 15: 1222-1223.*
Brenner, 1999, Trends in Genetics 15: 132-133.*
Bork et al., 1996, Trends in Genetics 12:425-427.*
GenBank Accession No. NP_004813, "netrin-1 precursor [*Homo sapiens*]", 2 pages, submitted May 7, 1999, first published Jan. 6, 2000, accessed May 3, 2011.
GenBank Accession No. NM_004822, "*Homo sapiens* netrin 1 (NTN1), mRNA", 3 pages, submitted May 7, 1999, first published Jan. 6, 2000, accessed May 3, 2011.
Hu, "Trascriptional regulation conferred through the 5\ untranslated region: RHOX5-mediated repression of the UNC5c netrin receptor gene in sertoil cells", Biology of Reproduction, 77:78a-78 (2007) abstract.
Lee, et al., "Extracellular guidance cues in regulating sperm motility", Fertility & Sterility, S365 (2007).
Mollet, et al., "A lily stylar pectin is necessary for pollen tube adhesion to an in vitro stylar matrix", The Plant Cell, 12:1737-1749 (2000).
Suarez, et al., "Sperm transport in the female reproductive tract", Human reproduction Update, 12(1):23-27 (2000).

* cited by examiner

*Primary Examiner* — Bridget E Bunner
*Assistant Examiner* — Christina Borgeest
(74) *Attorney, Agent, or Firm* — Pabst Patent Group LLP

(57) ABSTRACT

Methods and compositions for male or female contraception are provided. The compositions include an effective amount of netrin-1 to reduce or inhibit sperm concentration in semen of males or to inhibit or reduce fusion of male gametes with female gametes in a female subject Still another embodiment provides a method for diagnosing male infertility by determining the amount of netrin-1 in a sample of epididymal fluid or semen from a male subject, comparing the amount of netting-1 in the sample to levels of netrin-1 in samples of epididymal fluid or semen from fertile males, wherein levels of netrin-1 in the sample from the male subject that are higher or lower than levels of netrin-1 in samples from fertile males are indicative of male infertility in the male subject.

2 Claims, 5 Drawing Sheets

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: PCR Primer

<400> SEQUENCE: 1
ctgcaaccga tgtgccaaag                                              20

<210> SEQ ID NO 2
<211> LENGTH: 20
<212> TYPE: DNA
<213> ORGANISM: Artificial Sequence
<220> FEATURE:
<223> OTHER INFORMATION: PCR Primer

<400> SEQUENCE: 2
aaaacccctg acggccaagt                                              20
```

NETRIN-1 COMPOSITIONS AND METHODS OF USE THEREOF

CROSS REFERENCE TO RELATED APPLICATIONS

This application is a filing under 35 U.S.C. §371 of PCT/US2008/082238 filed with the United States Receiving Office of the Patent Cooperation Treaty on Nov. 3, 2008, which claims priority to U.S. Provisional Patent Application No. 61/001,580 filed Nov. 2, 2007, and where permissible is incorporated herein in its entirety.

FIELD OF THE INVENTION

Aspects of the invention are generally directed to cell biology, in particular to polypeptides affecting the biological activities of sperm.

BACKGROUND OF THE INVENTION

About 12 percent of women (7.3 million) in the United States aged 15-44 had difficulty getting pregnant or carrying a baby to term in 2002, according to the National Center for Health Statistics of the Centers for Disease Control and Prevention. In one third of cases, infertility is due to the man (male factors). Major etiological factors include ovulatory dysfunction, abnormal tubal function, cervical factors, and male sperm factors. (The Merck Manual of Diagnosis and Therapy, Merck Research Laboratories, 16th Ed., p. 1768-1770, (1992)). An estimated five to six percent of men in the reproductive age group are infertile. Most causes of male infertility are due to an abnormal sperm count or low semen quality.

A majority of problems associated with fertility in males stem from changes in testosterone levels. In particular, decreases in concentration of this steroid can result in infertility and impotence. Endogenous estrogen has been well-documented to serve as a regulatory factor in testosterone production by interaction with the estrogen receptor (Nozu, K. et al., *J. Biol. Chem.* 256, 1915 (1981); Brinkman, A. et al., *Endocrinology*, 110, 1834 (1982)). Unfortunately, hormone therapies can have serious side-effects.

Thus, it is an object of the invention to provide non-steroidal compositions and methods for treating male infertility.

It is another object of the invention to provide compositions and methods for decreasing sperm concentration in semen.

SUMMARY OF THE INVENTION

Methods and compositions for modulating spermiation in a male subject are provided. One embodiment provides a composition having an effective amount of netrin-1, a prodrug, or derivative thereof to increase spermiation when administered to a male subject relative to a control. The composition can be used to increase the concentration of sperm in the semen of the subject. Agonists of netrin-1 can also be used. Thus, methods for treating male infertility are also provided. Preferably, the methods use non-steroidal formulations.

Still another embodiment provides compositions and methods for decreasing the concentration of sperm in the semen of a subject. The composition includes an effective amount of a netrin-1 antagonist to decrease the concentration of sperm in the semen of the subject relative to a control. Representative netrin-1 antagonists include but are not limited to antibodies and antigen binding fragments thereof, inhibitory nucleic acids specific of netrin-1, and small molecule antagonists.

Another embodiment provides a female contraceptive composition comprising an effective amount of netrin-1 or a variant thereof to inhibit or reduce fertilization when administered to a female subject. Still another embodiment provides a method for inhibiting or preventing pregnancy by administering an effective amount of netrin-1 or a variant thereof to a female subject to inhibit or reduce fusion of male gametes with gametes of the female subject.

Still another embodiment provides a method for diagnosing male infertility by determining the amount of netrin-1 in a sample of epididymal fluid or semen from a male subject, comparing the amount of netrin-1 in the sample to levels of netrin-1 in samples of epididymal fluid or semen from fertile males, wherein levels of netrin-1 in the sample from the male subject that are higher or lower than levels of netrin-1 in samples from fertile males are indicative of male infertility in the male subject.

DETAILED DESCRIPTION OF THE INVENTION

I. Definitions

Figure 1:
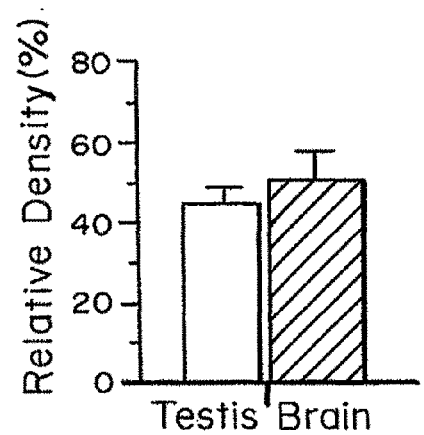
FIG. 1 is a bar graph showing the relative density of netrin-1 RNA in testis and brain in mouse.

The terms "individual", "host", "subject", and "patient" are used interchangeably herein, and refer to a mammal, including, but not limited to, murines, simians, humans, mammalian farm animals, mammalian sport animals, and mammalian pets.

The term "agent" or "therapeutic agent" is used to describe a compound that has or may have a pharmacological activity. Agents include compounds that are known drugs, compounds for which pharmacological activity has been identified but that are undergoing further therapeutic evaluation, and compounds that are members of collections and libraries that are to be screened for a pharmacological activity. The term includes an organic or inorganic chemical such a peptide, including antibodies, proteins and small molecules and natural products.

As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

II. Compositions and Methods of Use Thereof for Treating Male Infertility

It has been discovered that netrin-1 is a regulator of spermiation/spermatid release and sperm chemotaxis. Thus, one embodiment provides compositions containing netrin-1, netrin-1 agonists, netrin-1 variants, netrin-1 derivatives, or prodrugs thereof in an amount effective to increase spermination in a male subject. The compositions can be used to increase the concentration of sperm in semen in male subjects. Accordingly, methods for treating male infertility are also provided.

A. Netrin-1 Compositions

1. Netrin-1

Netrin-1 is expressed in adult mouse testis. It is enriched around elongated spermatids-adhesions sites between spermatids and sertoli cells. Cells expressing netrin-1 reduce spermatogoza attachment to the cell. Treatment of netrin-1 to the released spermatozoa in culture resulted in hyperactive mobility and calcium influx at the midpiece of spermatogoza. These results show a role of netrin-1 in regulating sperm adhesion and motility in culture. In vivo, suppression of netrin-1 expression by eletroporation of its miRNA in adult mouse testis leads to disorientation of germ cell patterning and accumulation of elongated spermatids. Over expression of netrin-1, on the other hand, causes early release/detachment of undifferentiated spermatocytes. Taken together, the date provided herein show that netrin-1, acting as a regulator of the cell adhesions between germ cell and sertoli cells in adult testis, plays an important role in sperm orientation, release, and motility.

Netrin-1 is a secreted extracellular protein, and has been previously identified as an axonal outgrowth promoting factor and an axon guidance cue. During axon pathfinding, a process essential for proper wiring in the brain during development, netrin-1 not only induces growth cone attraction, but also repulsive response, depending on the cellular membrane receptors. Two major classes of netrin-1 receptors have been identified: DCC and Unc5 families. While DCC is required for growth cone attraction, Unc5, on the other hand, seems to mediate the repulsive effect of netrin. In addition, other netrin-1 receptors, including integrins and DsCAM, have also been reported to regulate netrin-1 functions. In addition to axon pathfinding, netrin-1 has been reported to play an important role in regulating angiogenesis and mammary gland morphorgenesis during mouse development.

The protein sequence for human netrin-1 is known in the art and has GenBank Accession No. NP_004813. Similarly, the nucleic acid sequence for human netrin-1 is known and has GenBank Accession No. NM_004822.

2. Variants of Netrin-1

It will be appreciated that variants of netrin-1 can also be used in the disclosed compositions and methods of using the compositions. Exemplary variant netrin-1 polypeptides include, but are not limited to netrin-1 polypeptides that are mutated to contain a deletion, substitution, insertion, or rearrangement of one or more amino acids. Typically, the mutation increases or decreases one or more biological activities of netrin-1. In one embodiment the variant netrin-1 polypeptide has the same activity, substantially the same activity, or different activity as a reference netrin-1 polypeptide, for example a non-mutated netrin-1 polypeptide. Substantially the same activity means it retains the ability to regulate spermiation or sperm chemotaxis.

A variant netrin-1 polypeptide can have any combination of amino acid substitutions, deletions or insertions. In one embodiment, the netrin-1 variant polypeptides have an integer number of amino acid alterations such that their amino acid sequence shares at least 60, 70, 80, 85, 90, 95, 97, 98, 99, 99.5 or 100% identity with an amino acid sequence of a wild type netrin-1, preferably human netrin-1. In a preferred embodiment, netrin-1 variant polypeptides have an amino acid sequence sharing at least 60, 70, 80, 85, 90, 95, 97, 98, 99, 99.5 or 100% identity with the amino acid sequence of a wild type murine or wild type human netrin-1 polypeptide.

Percent sequence identity can be calculated using computer programs or direct sequence comparison. Preferred computer program methods to determine identity between two sequences include, but are not limited to, the GCG program package, PASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity. Exemplary parameters for amino acid sequence comparison include the following: 1) algorithm from Needleman and Wunsch (*J. Mol. Biol.*, 48:443-453 (1970)); 2) BLOSSUM62 comparison matrix from Hentikoff and Hentikoff (*Proc. Natl. Acad. Sci. U.S.A.*, 89:10915-10919 (1992)) 3) gap penalty=12; and 4) gap length penalty 4. A program useful with these parameters is publicly available as the "gap" program (Genetics Computer Group, Madison, Wis.). The aforementioned parameters are the default parameters for polypeptide comparisons (with no penalty for end gaps).

Alternatively, polypeptide sequence identity can be calculated using the following equation: % identity=(the number of identical residues)/(alignment length in amino acid residues)*100. For this calculation, alignment length includes internal gaps but does not include terminal gaps.

Amino acid substitutions in netrin-1 polypeptides may be "conservative" or "non-conservative". As used herein, "conservative" amino acid substitutions are substitutions wherein the substituted amino acid has similar structural or chemical properties, and "non-conservative" amino acid substitutions are those in which the charge, hydrophobicity, or bulk of the substituted amino acid is significantly altered. Non-conservative substitutions will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain.

Examples of conservative amino acid substitutions include those in which the substitution is within one of the five following groups: 1) small aliphatic, nonpolar or slightly polar residues (Ala, Ser, Thr, Pro, Gly); 2) polar, negatively charged residues and their amides (Asp, Asn, Glu, Gln); polar, positively charged residues (His, Arg, Lys); large aliphatic, non-polar residues (Met, Leu, Ile, Val, Cys); and large aromatic resides (Phe, Tyr, Trp). Examples of non-conservative amino acid substitutions are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

3. Peptidomimetics

Peptidomimetics are compounds which mimic the biological activity of peptides while offering the advantages of increased bioavailability, biostability, bioefficiency, and bioselectivity against the natural biological target of the parent peptide. One embodiment provides peptidomimetics of netrin-1. Peptidomimetics have general features analogous to their parent structures, polypeptides, such as amphiphilicity. Examples of such peptidomimetic materials are described in Moore et al., *Chem. Rev.* 101 (12), 3893-4012 (2001). As used herein, the term "peptidomimetic" includes chemically modified peptides and peptide-like molecules that contain non-naturally occurring amino acids, peptoids, and the like. Preferred substituents in peptidomimetic netrin-1 polypeptides include those which correspond to the backbone or side chains of naturally occurring netrin-1 polypeptides. Suitable classes of peptidomimetics include, but are not limited to peptoids, retro-inverso peptides, azapeptides, urea-peptidomimetics, sulphonamide peptides/peptoids, oligoureas, oligocarbamates, N,N'-linked oligoureas, oligopyrrolinones, oxazolidin-2-ones, azatides, and hydrazino peptides.

4. Prodrugs

Prodrugs of the disclosed compositions are also provided. These include prodrugs or netrin-1, antagonists of netrin-1, or agonists of netrin-1. Prodrugs are precursors of the active form of a drug. A prodrug must undergo chemical conversion by metabolic processes before becoming an active pharmacological agent. Typically a prodrug is made to increase bioavailability, permeability, or targeted absorption.

B. Netrin-1 Agonists

Compositions containing netrin-1 agonists are also provided. Netrin-1 agonists refers to agents that increase netrin-1 biological activity or increase expression of netrin-1. Typically small molecule agonists can obtained by screening a compound library for netrin-1 activity.

1. Expression Regulators

In one embodiment, regulators of netrin-1 expression are provided. These regulators increase the endogenous expression of netrin-1 in a subject. Exemplary molecules that increase the endogenous expression of netrin-1 include, but are not limited to transcription factors, 2. Netrin-1 Receptor Agonists A preferred embodiment provides netrin-1 receptor agonists. Receptors for netrin-1 are on sperm as demonstrated by the increase in intracellular calcium in sperm treated with netrin 1. Thus, agonist antibodies or small molecule compounds, typically less than 1000 daltons can be used to agonize the netrin-1 receptor. It is believed that agonizing the netrin-1 receptor on sperm will result in an increase in spermiation.

C. Methods for Treating Male Infertility

The disclosed compositions can be used in males to increase the number of sperm in semen. In a preferred embodiment, the disclosed netrin-1 or netrin-1 agonist compositions are administered to a male, preferably a human male, in an amount effective to increase spermiation relative to a control. Increasing spermiation can increase the concentration of sperm in semen. One factor in male infertility is a low concentration of sperm in the semen. Thus, by administering the disclosed compositions that increase spermiation, at least one symptom of male infertility can be treated.

During spermatogenesis, cell adhesions formed between germ cells and sertoli cells play important roles in germ cell adhesion, migration, differentiation, and release. Cell adhesions in seminiferous epithelium include ectoplasmic specializations, tight, gap, and desmosome-like junctions. Ectoplasmic specializations (ESs) are actin mediated cell adhesion complexes found at the apical region of the seminiferous epithelium in which spermatids anchor onto sertoli cells before their release into the lumen at spermiation and at the basal region of the seminiferous epithelium between sertoli cells. These ESs divide the microenvironment of the seminiferous epithelium into the basal and adluminal compartments. Spermatogonia and early spermatocytes, which are located in the basal compartment, are in contact with the basement membrane and sertoli cells, whereas differentiating spermatocytes and spermatids, which are located in the adluminal compartment, are in contact with only sertoli cells, therefore, receive nutrition, hormones, and local factors exclusively from sertoli cells. ESs are highly dynamic adhesive structures. The rapid turnover of ESs between sertoli cells at the basal region of the seminiferous epithelium is believed to allow the movement of preleptoten spermatocytes across the blood-testis barrier at stages VIII and IX of the cycle; whereas, the release of mature spermatids (spermatozoa) at the adluminal compartment is accomplished by the disassembly of ESs in the apical region.

In addition to ESs, the tubulobulbar complex (TC) is another testis specific form of actin based cell adhesion structure, surrounding the head of spermatids and protruding into the invagination of sertoli cell plasma membrane. Several functions of TC have been proposed. It may serve as an anchoring device to retain spermatids in the seminiferous epithelium before spermiation; it may be used to remove the linkage between sertoli cells and spermatids to permit the release of spermatids into the tubular lumen at spermiation; and it may also function as a protein cleavage center to eliminate excess aerosomal contents before spermiation. While these cell adhesions are functionally important during spermatogenesis and spermiation, the precise molecular components of both ES and TC began to be understood. Various cell adhesion molecules have been shown to be involved in the cell junction during spematogenesis. Among them, nectins, junctional adhesion molecular C (JAM-C), and members of the immunoglobulin super family (e.g., synCAM) have been shown to play essential roles in spermatogenesis. However, exactly how the turnover of these adhesions is regulated remains largely unclear.

The release of mature spermatozoa from the protective sertoli cells into the lumen of the seminiferous tubule is known as spermiation and includes removal of the remaining unnecessary cytoplasm and organelles. Spermatozoa then develop their motility and fertility during epididymal transport process to become a functional mature sperm. A mature sperm swims towards a gradient of a chemoattractant that is released by the oocyte. This process is essential for sperm fertilization, which has been studied in marine invertebrates with external fertilization (e.g., sea urchins) and been demonstrated in mammals (e.g., humans). However, in the absence of the chemoattractant and during epididymal transport process it is unclear how sperms/spermatozoa distinguish which direction to "swim", i.e. to seminiferous testis tubule or to the cauda epididymis.

The data in the Examples shows that netrin-1 plays a role in spermiation.

D. Diagnostics

Levels of netrin-1 in epididymal fluid or semen can be used as a diagnostic marker for male infertility. Levels of netrin-1 that are below or above levels of netrin-1 in fertile males are indicative of male infertility. One embodiment provides a method for diagnosis or assisting in the diagnosis of male infertility including obtaining a sperm sample from a male subject and analyzing the sample to determine the amount of netrin-1 present in the sample. Samples having more or less netrin-1 compared to the amount of netrin-1 present in samples from fertile male subjects is indicative of male infertility.

Methods of detecting proteins in a sample are known in the art and include, but are not limited to immunochemical techniques and spectroscopic techniques. In one embodiment, the amount of netrin-1 in a sample is determined using mass spectroscopy.

III. Contraceptive Compositions and Methods of Use Thereof

A. Female Contraceptives

It has been discovered that netrin-1 reduces or inhibits the ability of sperm to fertilize an egg or ovum. One embodiment provides a female contraceptive composition containing an effective amount of netrin-1 or variant thereof to inhibit or reduce the ability of sperm to fertilize an egg or ovum relative to a control. The composition is administered to a female subject after unprotected intercourse or insemination. The composition can be administered immediately after intercourse or from about 1 to 48 hours after intercourse, preferably about 24 hours after intercourse. In a preferred embodiment, the female contraceptive composition is administered orally in a unit dosage formulation.

Another embodiment provides a method for preventing pregnancy by administering an effective amount of netrin-1 or variant thereof to a female subject to inhibit fertilization of an egg or ovum.

Netrin-1 can be administered to a female subject in amounts effective to prevent fusion of male gametes with gametes of the female subject.

B. Male Contraceptives

Because netrin-1 has been discovered to play a role in spermiation and sperm motility, antagonists of netrin-1 can be used as a male contraceptive to reduce the concentration of sperm in semen. Thus, one embodiment provides a male contraceptive containing an antagonist of netrin-1. The antagonist can be an antibody that binds to netrin-1, a netrin-1 receptor blocker, or an inhibitory nucleic acid.

1. Antagonistic Antibodies to Netrin-1

Suitable antagonists of netrin-1 include, but are not limited to antibodies to netrin-1 or fragments of antibodies that bind netrin-1 and prevent it for interacting with other proteins, in particular with receptor molecules on sperm. Antibodies to netrin-1 are commercially available from a variety of sources. The antibodies can be polyclonal, monoclonal, humanized, linear, or fragments thereof capable of binding to netrin-1.

2. Netrin-1 Receptor Blockers

Another embodiment provides netrin-1 antagonists that bind to netrin-1 receptors on sperm and compete with endogenous netrin-1 for binding to the receptors. Such antagonists can be antibodies or fragments thereof that bind to the receptor on sperm but do not activate signal transduction through the receptor. Preferably the netrin-1 receptor blocker is a small organic molecule that out competes endogenous netrin-1 for binding to receptors on sperm.

3. Inhibitory Nucleic Acids

Still another embodiment provides inhibitory nucleic acids that down regulate netrin-1 expression in a subject. Inhibitory nucleic acids are known in the art and include antisense DNA, siRNA, and microRNA. In a preferred embodiment, the inhibitory nucleic acid is microRNA specific for netrin-1 mRNA.

4. Methods of Using Compositions for Male Contraception

Antagonists of netrin-1 can be used to decrease the concentration of sperm in semen of a subject. Typically an effective amount of a netrin-1 antagonist is administered to a male subject to decrease the concentration of sperm in the semen of the male subject. The amount and dosing regimen can be determined by those of ordinary skill in the art. Routes of administration are described more fully below with regard to pharmaceutical compositions.

IV. Pharmaceutical Compositions

Pharmaceutical compositions including netrin-1, netrin-1 agonists, and netrin-1 antagonists are provided. Pharmaceutical compositions containing peptides or polypeptides may be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration. The compositions may also be administered using bioerodible inserts and may be delivered directly to spinal structures, such as intervertebral discs, the epidural space and facet joints. The compositions can be formulated in dosage forms appropriate for each route of administration. Compositions containing netrin-1 agonists and netrin-1 antagonists that are not peptides or polypeptides can additionally be formulated for enteral administration.

The agonists and antagonists disclosed herein are administered to a subject in a therapeutically effective amount. As used herein the term "effective amount" or "therapeutically effective amount" means a dosage sufficient to treat, inhibit, or alleviate a symptom of male infertility in a subject in need thereof. Alternatively, and effective amount with regard to male contraception is one that reduces the concentration of sperm in semen. The precise dosage will vary according to a variety of factors such as subject-dependent variables (e.g., age, etc.), the injury or pathology being treated, and the treatment being effected.

For the netrin-1 agonists and antagonists disclosed herein, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the route of administration, and on the duration of the treatment desired. Generally dosage levels of 0.001 to 10 mg/kg of body weight daily are administered to mammals. Generally, for intravenous injection or infusion, dosage may be lower.

1. Formulations for Parenteral Administration

In one embodiment, netrin-1, netrin-1 agonists and antagonists including those containing peptides and polypeptides, are administered in an aqueous solution by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN 20, TWEEN 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Enteral Administration

Netrin-1 complex antagonists that are not peptides or polypeptides can also be formulated for oral delivery. Oral solid dosage forms are known to those skilled in the art. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the present proteins and derivatives. See, e.g., Remington's Pharmaceutical Sciences, 21st Ed. (2005, Lippincott, Williams & Wilins, Baltimore, Md. 21201) pages 889-964. The compositions may be prepared in liquid form, or may be in dried powder (e.g., lyophilized) form. Liposomal or polymeric encapsulation may be used to formulate the compositions. See also Marshall, K. In: Modern Pharmaceutics Edited by G. S. Banker and C. T. Rhodes Chapter 10, 1979. In general, the formulation will include the active agent and inert ingredients which protect peptide in the stomach environment, and release of the biologically active material in the intestine.

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. Netrin-1, netrin-1 agonists and antagonists can be incorporated into an inert matrix which permits release by either diffusion or leaching mechanisms, e.g., films or gums. Slowly disintegrating matrices may also be incorporated into the formulation. Another form of a controlled release is one in which the drug is enclosed in a semipermeable membrane which allows water to enter and push drug out through a single small opening due to osmotic effects. For oral formulations, the location of release may be the stomach, the small intestine (the duodenum, the jejunem, or the ileum), or the large intestine. Preferably, the release will avoid the deleterious effects of the stomach environment, either by protection of the active agent (or derivative) or by release of the active agent beyond the stomach environment, such as in the intestine. To ensure full gastric resistance an enteric coating (i.e, impermeable to at least pH 5.0) is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac.

V. Methods for Screening for Modulators of Netrin-1

Methods for identifying modulators of the function, expression, or bioavailability of netrin-1 in spermiation, homologues thereof, and receptors of netrin-1 can be accomplished using well known techniques and reagents. The modulator can modulate the netrin-1 signaling pathway, for example to inhibit or reduce netrin-1 signaling by interacting with netrin-1 or by interfering with netrin-1 binding to a netrin-1 receptor. Modulation of netrin-1 can be direct or indirect. Direct modulation refers to a physical interaction between the modulator and netrin-1 mRNA, protein, or DNA. Indirect modulation of netrin-1 can be accomplished when the modulator physically associates with a cofactor, second protein or second biological molecule that interacts with netrin-1 mRNA, DNA or protein either directly or indirectly. Additionally, indirect modulation includes modulators that affect the expression or the translation of RNA encoding netrin-1.

In some embodiments, the assays can include random screening of large libraries of test compounds. The test compounds are typically, non-protein small molecules. The term "small molecule" refers to compounds less than 1,000 daltons, typically less than 500 daltons. Alternatively, the assays may be used to focus on particular classes of compounds suspected of modulating the function or expression of netrin-1 or homologues thereof in cells, tissues, organs, or systems.

Assays can include determinations of netrin-1 expression, protein expression, protein activity, signal transduction, or binding activity. Other assays can include determinations of netrin-1 nucleic acid transcription or translation, for example mRNA levels, mRNA stability, mRNA degradation, transcription rates, and translation rates.

In one embodiment, the identification of a netrin-1 modulator is based on the function of netrin-1 in the presence and absence of a test compound. The test compound or modulator can be any substance that alters or is believed to alter the function of netrin-1, in particular the function of netrin-1 in the netrin-1 signaling pathway. Typically, a modulator will be selected that reduces, eliminates, or inhibits netrin-1 mediated signaling or increases or enhances apoptosis of cancer cells expressing netrin-1.

One exemplary method includes contacting netrin-1 protein with at least a first test compound, and assaying for an interaction between netrin-1 and the first test compound with an assay. The assaying can include determining inhibition of netrin-1 pro-apoptotic signaling, cell survivability, or lifespan assays.

Specific assay endpoints or interactions that may be measured in the disclosed embodiments include assaying for netrin-1 cell signaling or lifespan modulation, down or up regulation or turnover. These assay endpoints may be assayed using standard methods such as FACS, FACE, ELISA, Northern blotting and/or Western blotting. Moreover, the assays can be conducted in cell free systems, in isolated cells, genetically engineered cells, immortalized cells, or in organisms such as transgenic animals.

Other screening methods include using labeled netrin-1 to identify a test compound, netrin-1 can be labeled using standard labeling procedures that are well known and used in the art. Such labels include, but are not limited to, radioactive, fluorescent, biological and enzymatic tags.

Another embodiment provides a method for identifying a modulator of netrin-1 expression by determining the effect a test compound has on the expression of netrin-1 in cells. For example isolated cells or whole organisms expressing netrin-1 or both can be contacted with a test compound. netrin-1 expression can be determined by detecting protein expression or netrin-1 or netrin-1 mRNA transcription or translation. Suitable cells for this assay include, but are not limited to, cancer cells, immortalized cell lines, primary cell culture, or cells engineered to express netrin-1, for example cells from mammals such as humans. Compounds that modulate the expression of netrin-1, in particular that reduce or inhibit netrin-1 cell signaling, can be selected.

Another embodiment provides for in vitro assays for the identification of netrin-1 modulators or modulators of netrin-1 homologues. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule, for example a nucleic acid encoding netrin-1 or netrin-1 protein, in a specific fashion is strong evidence of a related biological effect. Such a molecule can bind to a netrin-1 nucleic acid and modulate expression of netrin-1. The binding of a molecule to a target may, in and of itself, be inhibitory, due to steric, allosteric or charge—charge interactions or may downregulate or inactivate netrin-1. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

Other embodiments include methods of screening compounds for their ability to modulate netrin-1 function or homologues thereof in cells. Various cell lines can be utilized for such screening assays, including cells specifically engineered for this purpose. Suitable cells include cancer cells that express netrin-1. Cells can also be engineered to express netrin-1 or a modulator thereof. Furthermore, those of skill in the art will appreciate that stable or transient transfections, which are well known and used in the art, may be used in the disclosed embodiments.

For example, a transgenic cell comprising an expression vector can be generated by introducing the expression vector into the cell. The introduction of DNA into a cell or a host cell is well known technology in the field of molecular biology and is described, for example, in Sambrook et al., Molecular Cloning 3rd Ed. (2001). Methods of transfection of cells include calcium phosphate precipitation, liposome mediated transfection, DEAE dextran mediated transfection, electroporation, ballistic bombardment, and the like. Alternatively, cells may be simply transfected with the disclosed expression vector using conventional technology described in the references and examples provided herein. The host cell can be a prokaryotic or eukaryotic cell, or any transformable organism that is capable of replicating a vector and/or expressing a heterologous gene encoded by the vector. Numerous cell lines and cultures are available for use as a host cell, and they can be obtained through the American Type Culture Collection (ATCC), which is an organization that serves as an archive for living cultures and genetic materials (www.atcc.org).

A host cell can be selected depending on the nature of the transfection vector and the purpose of the transfection. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (Stratagene, La Jolla, Calif.). Alternatively, bacterial cells such as E. coli LE392 could be used as host cells for phage viruses. Eukaryotic cells that can be used as host cells include, but are not limited to, yeast, insects and mammals. Examples of mammalian eukaryotic host cells for replication and/or expression of a vector include, but are not limited to, HeLa, NIH3T3, Jurkat, 293, Cos, CHO, Saos, and PC12. Examples of yeast strains include YPH499, YPH500 and YPH501. Many host cells from various cell types and organisms are available and would be known to one of skill in the art. Similarly, a viral vector may be used in conjunction with either an eukaryotic or prokaryotic host cell, particularly one that is permissive for replication or expression of the vector. Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

In vivo assays involve the use of various animal models, including non-human transgenic animals that have been engineered to have specific defects, or carry markers that can be used to measure the ability of a test compound to reach and affect different cells within the organism. Due to their size, ease of handling, and information on their physiology and genetic make-up, mice are a preferred embodiment, especially for transgenic animals. However, other animals are suitable as well, including C. elegans, rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more test compounds are administered to an animal, and the ability of the test compound(s) to alter one or more characteristics, as compared to a similar animal not treated with the test compound(s), identifies a modulator. Other embodiments provide methods of screening for a test compound that modulates the function of netrin-1. In these embodiments, a representative method generally includes the steps of administering a test compound to the animal and determining the ability of the test compound to reduce one or more characteristics of aging, lifespan, or age-related disorder.

Treatment of these animals with test compounds will involve the administration of the compound, in an appropriate form, to the animal. Administration will be by any route that could be utilized for clinical or non-clinical purposes, including, but not limited to, oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

EXAMPLES

Example 1

Netrin-1 Expression in Adult Mouse Testis

Antibodies and Cells

Monoclonal antibodies were purchased as follows: anti-Netrin-1 from Sigma, anti-Myc (9e10) from Santa Cruz (Santa Cruz, Calif.). Goat anti-DCC was from Santa Cruz (Santa Cruz, Calif.). Stable HEK 293 cells expressing human netrin-1 were described as previously. Unless otherwise indicated, ~200 ng/ml human netrin-1 was used for stimulation. C57/BL6 mice were used.

Cell Culture and Transfection

HEK 293, Cos-7, and testicular cells were maintained in DMEM supplemented with 10% fetal calf serum, 100 Units/ml penicillin G and streptomycin (GIBCO). Cells were plated at a density of $10^6$ cells per 10-cm culture dish and allowed to grow for 12 hr before transfection using the calcium phosphate precipitation method for HEK293 or Cos-7 cells, and using electroporation for TC4 cells. Thirty-six hours after transfection, cells were lysed in modified RIPA buffer (50 mM Tris-HCl, pH 7.4, 150 mM sodium chloride, 1% NP40, 0.25% sodium-deoxycholate, and proteinase inhibitors)[27]. Lysates and/or medium were subjected to immuno-blotting analysis.

RT-PCR Analysis

Total RNAs were isolated from the testis of adult mice (p60) using Trizol (Invitrogen). Three micrograms of RNA were reverse transcribed into cDNA using Superscript III first-strand synthesis system (Invitrogen). One micro liter of cDNA was subjected to PCR amplification with the sequence specific primers (mouse netrin-1, 5'-ctgcaaccgatgtgccaaag-3' (SEQ ID NO:1) and 5'-aaaaccoctgacggccaagt-3' (SEQ ID NO:2). PCR reactions were performed in triplicate for each cDNA, and normalized to endogenous GADPH transcripts. Quantitative real time RT-PCR was carried out by using the Bio-Rad iCycler according to the manufacturer's instructions.

In Situ Hybridization

Testis tissues were removed from perfused mice, and re-fixed with 4% paraformaldehyde before cutting. Testis sections cut by a freezing microtome were then subjected to the treatment for the hybridization. The digoxigen (DIG) labeled riboprobes (sense and antisense) for netrin-1 were generated by in vitro transcription using their cDNA templates in the presence of DIG-UTP (DIG RNA Labeling Mix, Roche). DIG was visualized with the anti-DIG antibody coupled to the alkaline phosphatase (AP) using nitro blue tetrazolium/bromo-chloro-indolyl phosphate (NBT/BCIP) as a chromogen/substrate system.

Histological and Immunohistochemical Analyses in Mouse Testis

Mouse Testis was fixed in Bouin's fixative. Paraffin-embedded sections were de-paraffinization in xylene, dehydration through a graded ethanol series, and subjected to hematoxylin and eosin staining for their histological examination and immunohistochemical analysis. For HRP based immunohistochemical staining, endogenous peroxidase was blocked by incubation with 3% $H_2O_2$ in PBS for 10 min prior to immunostaining, and the immunoreactivity was examined by a DAB reaction performed according to the manufacturer's instructions (DAB conjugate Histomarker kit, invitrogen, Inc, CA). For immunofluorescence staining, in addition to antibodies, nuclei were labeled by Topro3 (invitrogen), and immunoreactivities were examined under a confocal microscope (Zeiss, Germany). The following primary antibodies were used: anti-Netrin-1 (monoclonal mouse, Sigma), anti-ZO-1 (rabbit polyclonal, Zymed Co.), anti-TP2 or anti-PRM2. Non-specific IgG anti-rabbit or mouse antibodies were used as negative controls.

Primary Culture of Germ and Sertoli Cells and Immunostaining

Decapusulated testes were placed in a plastic culture dish and cut into small fragments. Fragmented seminiferous tubules were incubated in a solution containing 2 µg/ml collagenase (Type I, C-2674, Sigma, St. Louis, Mo.), 1 µg/ml hyaluronidase (Sigma), 10 µg/ml DNase I (Sigma), and 1 µg/ml soybean trypsin inhibitor for 30 min at 32° C. Dissociated testicular cells were centrifuged at 1,500 rpm for 10 min, washed twice in DMEM/F12 medium containing 10% FBS (Gibco BRL, Grand Island, N.Y.). Following adjustment of cell concentration at $1 \times 10^6$ cells/ml with medium (DMEM/F12) containing 10% fetal bovine serum, testicular cells were cultured onto the coated glass coverslips for 6~8 hour at 32° C.

For culture of spermatogozoa isolated from epididymis, epididymis tissues, divided into caput and cauda epididymis, were punctured with a 27-gauge needle several times on plastic Petri dish (35 mm). Sperms were gently pull up to the washing media on the dish and incubated in the slide warmer at 25° C. for 10~15 min. The medium containing motile sperm was aspirated and placed in a 1.5-ml micro-centrifuge tube (Fisher), washed and sperm numbers were diluted to $1 \sim 10 \times 10^6$/ml by further addition of medium.

For immunostaining, testis cells or sperms isolated from epididymis were fixed with 4% paraformaldehyde or −20° C. methanol for 20 min, permeated, blocked with 5% bovine serum, and incubated with primary antibodies. Double-labeled immunostaining was done with appropriate fluorochrome-conjugated secondary antibodies. Images were taken on a Zeiss fluorescence microscope at 63×.

Results

To investigate potential functions of netrin-1 in germ cells, netrin-1 expression in mouse testis were examined. RT-PCR analysis showed that netrin-1 transcript was detected in adult mouse testis (P60, postnatal day 60), at a comparable level as that in the brain. Western blot analysis demonstrated that netrin-1 protein was indeed expressed in developing mouse testis, including adult testis, as a similar level as that detected in adult mouse brain (FIG. 1).

The distribution of netrin-1 transcript and protein during spermatogenic development in adult mouse testis was investigated using both in situ hybridization and immunohistochemical staining analyses. Positive signals were detected in nearly 100% of the seminiferous tubules using the antisense, but not sense, probes, indicating the specificity of the in situ hybridization analysis. Analysis of magnified images of the seminiferous tubules showed that netrin-1 transcripts were localized in sertoli cells (SCs) and in fractions (~30%) of round (RS) and elongated spermatids (ES), but not or at low/undetectable level in spermatogonium (Sg). Interestingly, immunohistochemical analysis showed that netrin-1 protein was mainly detected in regions, possible adhesion sites, between sertoli cells and mature sperms (in both RS and ES) of adult mouse testis. This immunoreactivity was not detected using nonspecific IgG antibody, suggesting the specificity. The high level of netrin-1 protein distributed around mature sperm head regions was noted and further confirmed by co-immunofluorescence staining analysis using antibodies against netrin-1 and transition protein-2 (TP-2), a marker for ES sperm head. These results demonstrate that netrin-1 is highly expressed in and largely distributed around mature sperms of adult mouse testis.

Example 2

Netrin-1 Regulation of Spermatozoa Movement

Sperm Choice Assay

The separation of spermatozoa by choice assay for chemotaxis analysis was performed in a four-drop mineral oil covered dish. The central well was filled with 100 µL sperm suspension and the crosses over each slide were filled with an equal volume of control media or netrin-1 media. The separation drop dish was put into an incubator (5% $CO_2$ atmosphere, 37° C.), allowed spermatozoa to migrate from the central to the each drop. We counted each group of sperms time dependently.

Analysis of Sperm Motility

Collected motile sperms from caput or cauda epididymis were placed on an uncoated glass-bottomed 3.5-mm dish containing the control or netrin-1 media (~$10^5$/ml). The movement of spermatozoa was observed for 5 to 20 minutes on the 37° C. temperature control chamber of Delta vision system using differential interference contrast optics with a 40× objective (Olympus Inc).

Results

Figure 2:
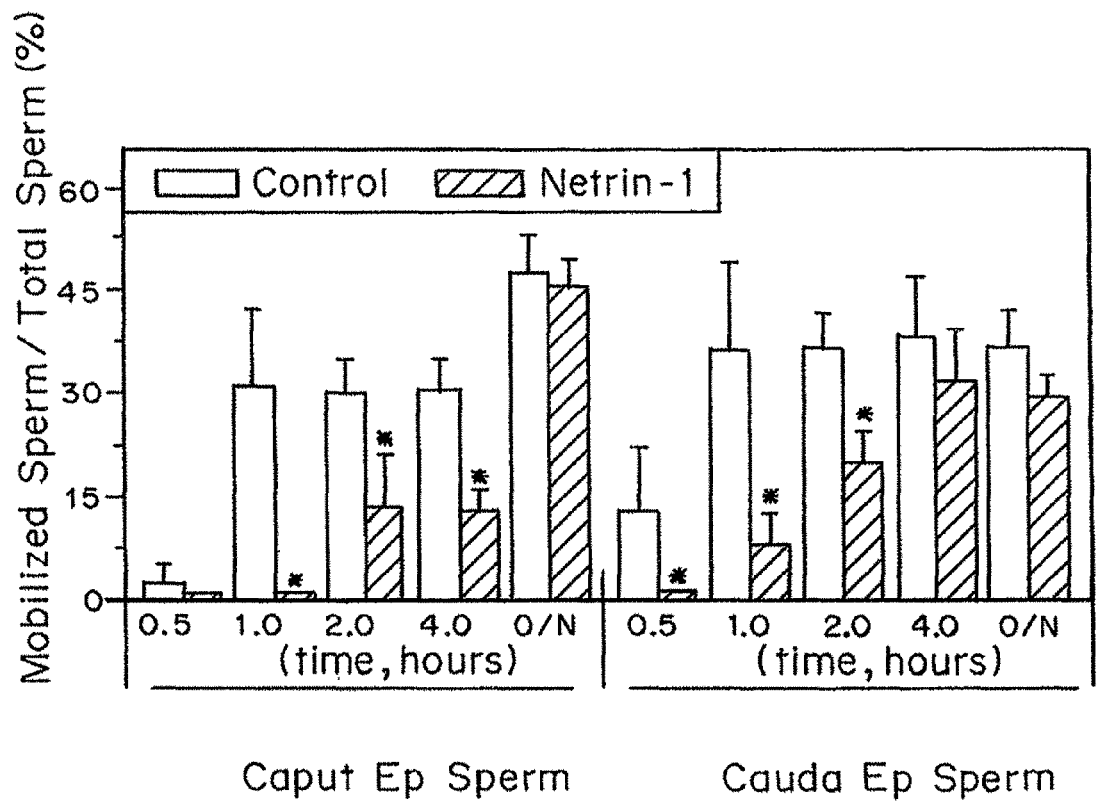
FIG. 2 is a bar graph of mobilized sperm/total sperm (%) versus time (hours) of sperm from caput epididymis or cauda epididymis treated with netrin-1 medium (darker shading) or control medium (lighter shading).

To test if netrin-1 plays a role in spermatozoa chemotaxis response, a choice assay that has been used for the analysis of sperm chemotaxis previously was used. The central well of the culture dish was filled with 10 μL of sperm suspension isolated from caput or caude epididymis, and equal volumes of control or netrin-1 media were applied to points on each side in cross design. After incubation at the indicated times, numbers of sperm in each location were counted. Note that after about 1 hour of incubation, significant numbers of caput (30%) or cauda (35%) spermatozoa moved to the control media side, but not to the site of netrin-1 medium (FIG. 2). At about 2 hours of incubation, the control media side still had a significantly higher number of sperm than that of netrin-1 media side (FIG. 2). However, after over night incubation, both caput or cauda sperms appeared to move to both control and netrin-1 containing sides (FIG. 2), losing the directional preference that may be due to the diffusion of netrin-1. These results suggest that netrin-1 may play a "repulsive" role in guiding spermatozoa movement, consistent with a role for netrin-1 in inhibition of spermatozoa attachment to the testis or sertoli cells and in release of elongated spermatids from testis/sertoli cells.

Whether netrin-1 protein regulates the motility of spermatozoa was investigated using time lapse imaging analysis. The sperm isolated from caput (C1) or cauda (C2) epididymis, when exposed to the control medium, moved as a "fish-swim" or progressive moving pattern towards one direction (called directional movement). The speed of the movement of caput spermatozoa was much slower than that of cauda sperm, with an average speed of ~40 μm/s and ~100 μm/s for caput and cauda sperms, respectively, consistent with previous reports. When exposed to netrin-1 medium, both caput and cauda sperms mobilized as an asymmetric flagellar beating pattern (a circular movement with a speed of ~73 μm/s and ~53 μm/s for caput and cauda sperms, respectively). These results suggest that netrin-1 not only regulates the speed of sperm motility, but also the direction of sperm movement in culture.

Example 3

Netrin-1 Induction of Calcium Flux of Spermatogozoa

Calcium Imaging Analysis

The spermatogozoa isolated from caput or cauda epididymis were collected in a 1.5 ml tube, washed, adjusted to $1 \times 10^6$-$3 \times 10^6$ sperms/ml, and incubated for 30 minutes at 37° C. in an atmosphere of 5% $CO_2$ for sperm capacitation. Capacitated sperm were washed by Ca, Mg Free PBS, loaded with 10 μM film 4-AM 0.05% Pluronic F-127 for 30 min, and replaced on a poly L lysine-coated glass-bottomed 3.5-mm dish (Iwaki) containing 100~200 μl of Ca, Mg Free PBS buffer. Control media or netrin-1 media were applied gently at the edge of the dish. Time-lapse images of [$Ca^{2+}$]i induced by netrin-1 (NM) and control media (CM) were recorded. DIC optics and the 488-nm wavelength beam of laser for excitation from a confocal microscope (optical lens 40× objective, Zeiss LSM 510) were used for examination. $Ca^{2+}$ influx intensity was measured and analyzed by Zeiss LSM 510 META image browser.

Results

Figure 3:
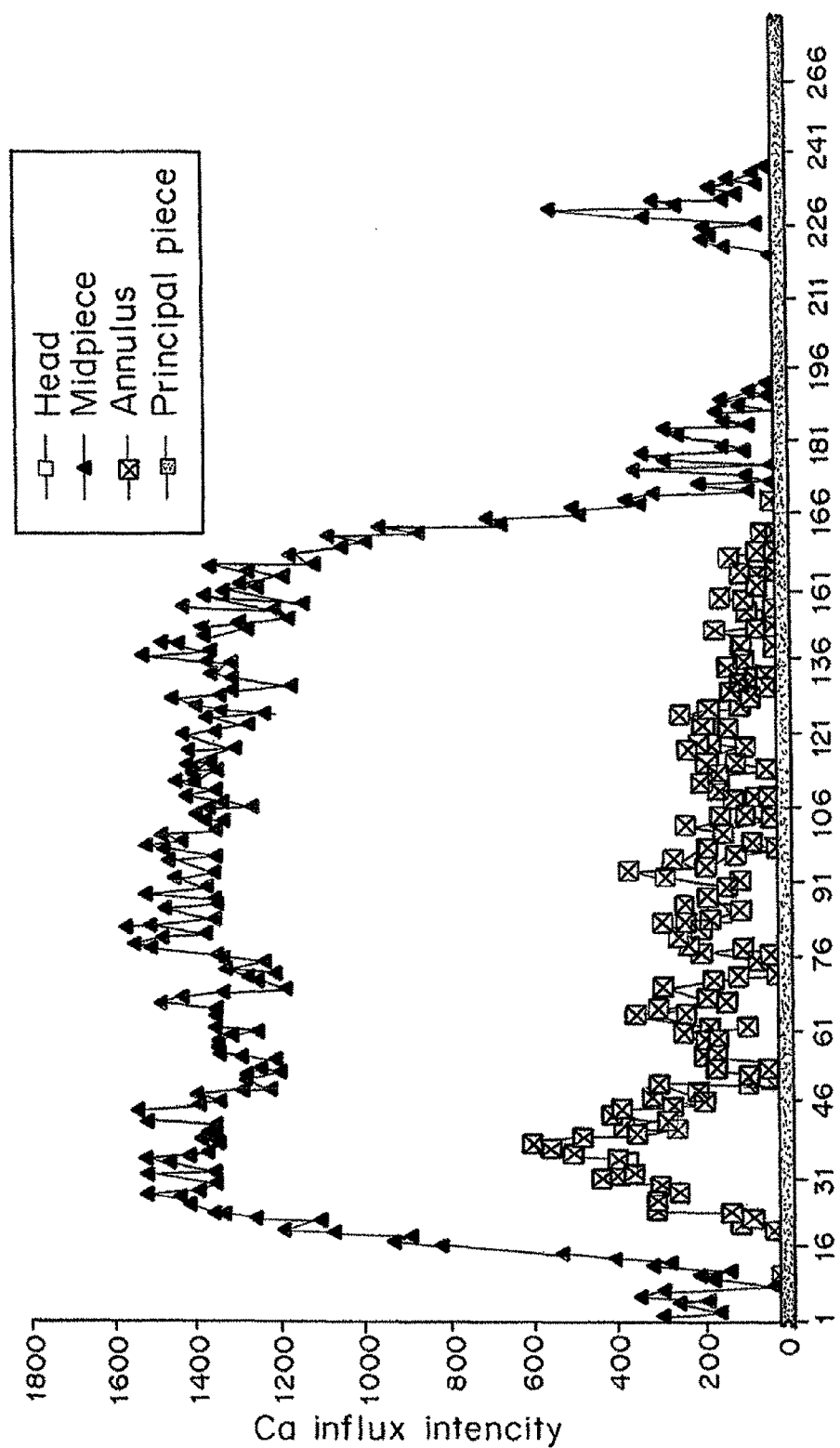
FIG. 3 is a line graph of calcium influx intensity versus the length of a sperm. The top trace is for the midpeice and the lower trace represents the annulus. Signal from the Head and Principal Piece were undetectable.
Figure 4:
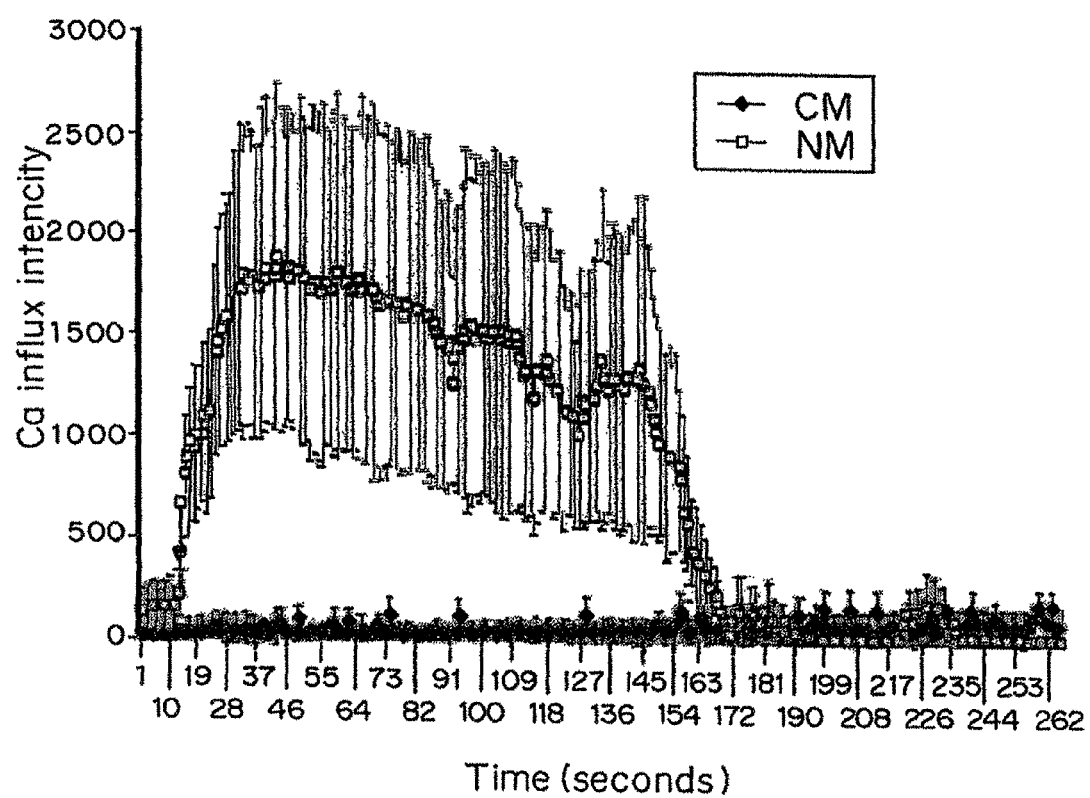
FIG. 4 is a line graph of calcium influx intensity versus time (seconds) of caput epididymis sperm treated with netrin-1 medium (NM (■)) or control medium (CM (♦)).
Figure 5:
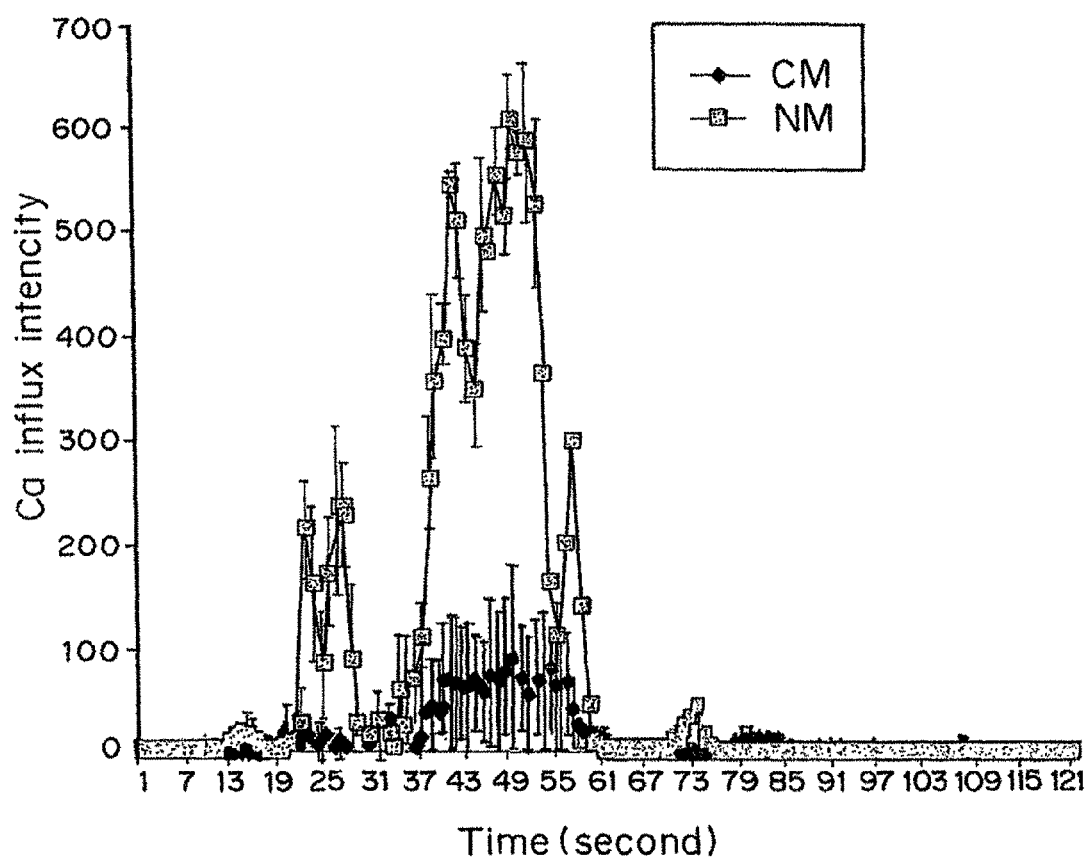
FIG. 5 is a line graph of calcium influx intensity versus time (seconds) of cauda epididymis sperm treated with netrin-1 medium (NM (■)) or control medium (CM (♦)).

Because an increase of intracellular $Ca^{2+}$ has frequently been associated with sperm flagellar-beat mode and chemotaxis, whether netrin-1 regulates $Ca^{2+}$ influx in spermatozoa was investigated. Spermatozoa isolated from mouse caput or cauda epidymis were treated with control or netrin-1. A significant increase in intracellular $Ca^{2+}$ in sperm from caput epidymis was observed in response to netrin-1, but not control medium. This netrin-1 response appeared to be spatial and time dependent event. The increased calcium was mainly observed in regions of the midpiece and annulus, but not in the head and tail regions of the sperm (FIG. 3). Intracellular $Ca^{2+}$ was observed immediately after netrin-1 treatment (~10 second), reached to the peak at ~30 seconds, and decreased at ~150 seconds (FIG. 4). Netrin-1 stimulation also caused an increase in intracellular $Ca^{2+}$ in cauda epididymal sperm (FIG. 5). However, this response appeared to be different from that observed in caput epididymal sperm. A majority of cauda sperm responded to netrin-1 in a "spike" pattern (FIG. 5).

These results demonstrate that netrin-1 may, via increased $Ca^{2+}$, enhance flagellar beating asymmetric movement of caput or caude sperms.

Example 4

Netrin-1 Regulation of Mature Sperm Distribution/Release in Adult Mouse Testis

Sperm-Cell (e.g., Sertoli or Cos-7 Cell) Attachment Assay

Cos-7 or TC Cells were transiently transfected with Netrin-1-IRES-EGFP plasmid by a modified calcium phosphate transfection method. The transfected cells were then co-cultured with sperms isolated from caput or cauda epididymis. The movement of spermatozoa stained with DRAQ5(1~10 μM) was recorded by time lapse imaging (for 5 min) on the 37° C. stage of a Carl Zeiss LSM510 META confocal microscope using differential interference contrast optics with a 63× objective (an argon excitation laser: 488/633 nm; Carl Zeiss Inc). The number of sperms around GFP expressing Cos-7 or TC cells in the radius circle were then counted.

Expression Constructs

The cDNAs encoding chicken netrin-1 were amplified by PCR and subcloned into mammalian expression vectors (pcDNA3-Mychis and pCAGGS-IRES-GFP). The authenticity of all constructs was verified by DNA sequencing. miRNA expression vectors were generated by the BLOCK-iT™ Lentiviral miR RNA Expression System (Invitrogen) according to the manufacturer's instruction. Briefly, mouse netrin-1 sequence was analyzed by a program provided by Invitrogen, and three regions were picked and cloned into pcDNA™6.2-GW/EmGFP-miR expression vector to yield pcDNA™6.2-GW/EmGFP-miR-Netrin-1. They were co-transfected with Myc-tagged netrin-1 construct into HEK 293 cells. Effective clones were identified based on their ability to suppress netrin-1 expression by Western blot analysis and further confirmed by immunostaining. The sequences for the miRNA-netrin-1 constructs are as follows.

In Vivo Electroporation

Adult Mice (P60) were anesthetized, and the testis was exposed under a dissecting microscope. A small hole made by a needle in the tunica, and then 20 μl per testis of plasmid DNA solution, to which 0.04% Trypan blue dye had been added to monitor the accuracy of the injection, was injected into the interstitial space of the testis. After DNA injection, EP was performed with an electroporator (Electrosequare Porator T820; BTX, San Diego, Calif.). Testes were held between a tweezers-type electrode, and square electric pulses were applied four times at 35 V with a constant time of 50 msec. All electroporation material was kept in ice including plasmid solutions, injection syringe and electroporatrode. These treatments produced no noticeable damage on testes by histopathological examination. After EP treatment, the skin was stitched, and the mice were allowed to recover and maintained until analysis.

Results

Figure 6A:
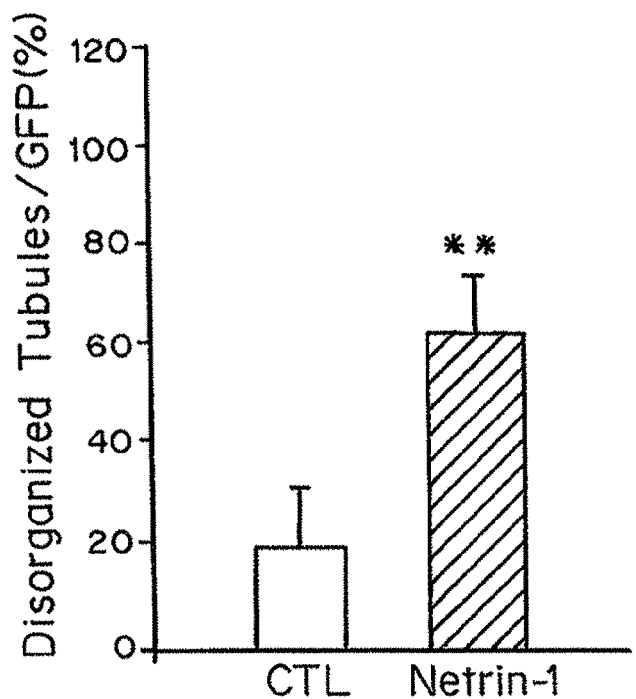
FIG. 6A is a bar graph of disorganized tubules/GFP (%) for control (CTL) or netrin-1.
Figure 6B:
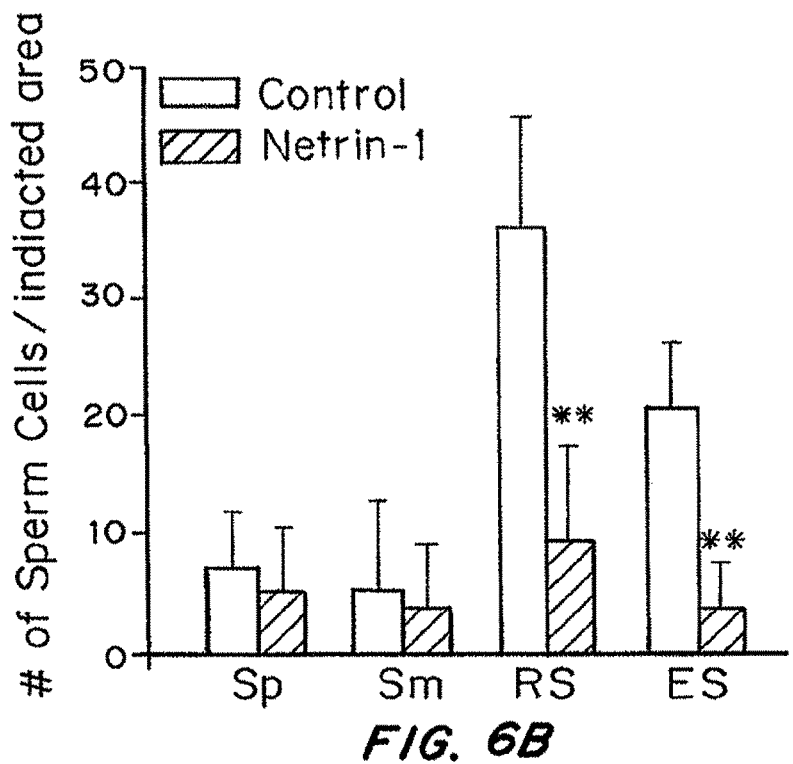
FIG. 6B is bar graph showing the number of sperm cells/indicated area with control on the left and netrin-1 treatment on the right for each area. Round Spermatids (RS), Elongated Spermatids (ES).

To investigate the role of netrin-1 in vivo and to determine if netrin-1 regulates elongated spermatid attachment to or release from sertoli cells/testis, miRNA-netrin-1 was expressed in adult mouse testis by in vivo eletroporation. To this end, plasmids encoding the scramble miRNA and miRNA-netrin-1 were injected and electroporated into the left and right side of adult mouse testis (P60), respectively. Animals were allowed to recover for thirty days after electroporation to allow recovery of the testis. Thirty days after electroporation, testis were collected and subjected for the phenotypic examination. The miRNA-netrin-1, but not the scramble miRNA, suppressed the expression of netrin-1 in mouse testis efficiently (FIG. 6A). Seminiferous tubules expressing the scramble miRNA (indicated by GFP) showed a normal spermatogenesis and normal distribution pattern of the spermatids (FIG. 6B), suggesting minimal, if there is any, damage of the testis by eletroporation. Remarkably, knockdown of netrin-1 by its micro RNA led to a mis-targeting or disorientation of spermatids (e.g., elongated spermatids). Further analysis by H & E staining shows that about 60% of miRNA-netrin-1 expressing tubules exhibited mis-targeting or altered distribution of sperms without a cavity formed in the central of the tubules. These results suggest a role of netrin-1 in regulating the distribution/targeting of spermatids.

To determine if netrin-1 regulates mature spermatid differentiation, the seminiferous tubules were examined by immuno-staining analysis with markers for mature spermatids. TP2 was detected in the seminiferous tubules expressing miRNA-netrin-1, however, it was mis-targeted or disoriented. Immunostaining of FAK, another protein distributed around mature sperms, was reduced specifically at the sites of elongated spermatids, but not round spermatids, in seminiferous tubules expressing miRNA-netrin-1. Taken together, these results indicate that netrin-1 appeared to be required for mature spermatid targeting/distribution, but not mature sperm differentiation.

Over expression of netrin-1 was investigated to determine if netrin-1 regulates mature sperm distribution/differentiation in vivo. The control EGFP and plasmid encoding netrin-1 (Netrin-1-IRES-EGFP) were electroporated into the left and right side of the testis of the same mouse (p60), respectively. Surprisingly, upon over expression of netrin-1, the majority (about 60%) of the netrin-1 expressing tubules showed an enlarged cavity of the tubules and reduced mature sperm numbers (both RS and ES) significantly. This phenotype may be caused by over expression or mis-expression of netrin-1 by eletroporation that induce the detachment of mature sperm from the tubules/sertoli cells. Such a result indicates that netrin-1 plays a role in regulation of the release or detachment of mature sperm in vivo.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for decreasing the concentration of sperm in semen comprising
   administering to a male an effective amount of a netrin-1 antagonist to decrease the concentration of sperm in semen relative to a control, wherein the netrin-1 antagonist is a netrin-1 antibody or antigen binding fragment that binds wild-type netrin-1.

2. The method of claim 1 wherein the antagonist is a netrin-1 antibody that binds wild-type netrin-1.

* * * * *